(12) United States Patent
Kirby et al.

(10) Patent No.: US 6,339,043 B1
(45) Date of Patent: Jan. 15, 2002

(54) METHOD AND COMPOSITION

(75) Inventors: Andrew Francis Kirby, Footscray; Rodney Walter Parr, Doncaster; Phillip Robert Tudor, Eldwood; David Hayshiv Parris, Parkville, all of (AU)

(73) Assignee: Huntsman Surfactants Technology Corporation, Salt Lake City, UT (US)

( * ) Notice: Subject to any disclaimer, the term of this patent is extended or adjusted under 35 U.S.C. 154(b) by 0 days.

(21) Appl. No.: 09/529,479

(22) PCT Filed: Oct. 14, 1998

(86) PCT No.: PCT/AU98/00852

§ 371 Date: Jul. 25, 2000

§ 102(e) Date: Jul. 25, 2000

(87) PCT Pub. No.: WO99/18785

PCT Pub. Date: Apr. 22, 1999

(30) Foreign Application Priority Data

Oct. 14, 1997 (AU) .............................................. PO9765

(51) Int. Cl.$^7$ .............................................. A01N 25/30
(52) U.S. Cl. ...................... 504/234; 504/330; 504/363; 514/772.6; 514/937
(58) Field of Search ................. 504/234, 330, 504/363; 514/772.6, 937

(56) References Cited

U.S. PATENT DOCUMENTS

| | | | |
|---|---|---|---|
| 4,191,680 A | | 3/1980 | Wegmann et al. ............. 260/42 |
| 4,435,383 A | * | 3/1984 | Wysong ........................ 424/78 |
| 4,867,972 A | | 9/1989 | Girardeau et al. ............. 424/81 |
| 5,631,309 A | * | 5/1997 | Yanagi et al. ................ 523/160 |

FOREIGN PATENT DOCUMENTS

| | | |
|---|---|---|
| EP | 201417 B1 | 9/1988 |
| FR | 2 397 444 | 2/1979 |
| FR | 2 545 325 | 5/1983 |
| JP | 58-131903 | 8/1983 |
| JP | 61-236701 | 10/1986 |
| JP | 62-36302 | 2/1987 |
| JP | 6 9302 | 1/1994 |

OTHER PUBLICATIONS

Abstract of JP 58131903, Aug. 6, 1983.
Abstract of JP 61236701, Oct. 22, 1986.
Abstract of JP 62036302, Feb. 17, 1987.
Abstract of FR 2545325, Nov. 9, 1984.

Derwent Abstract No. 1985–035826, of JP 59231001A, Dec. 25, 1984.
Nabeya and Yonemura, "Aqueous Pesticide Suspensions Containing Polycarboxylate Surfactants," *Chemical Abstracts* vol. 120 No.:238283r, 1994.
"Part 180–Tolerances and Exemptions from Tolerances for Pesticide Chemicals in or on Raw Agricultural Commodities," Federal Register, vol. 37, No. 164–Wednesday, Aug. 23, 1972, p. 16938.
Derwent Abstract No. 1985–035826, of JP 59–231001A, Dec. 1984.*

* cited by examiner

*Primary Examiner*—S. Mark Clardy
(74) *Attorney, Agent, or Firm*—SEED Intellectual Property Law Group PLLC

(57) ABSTRACT

A method of dispersing an insoluble material in an aqueous solution comprising the following steps:

(i) providing a formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and

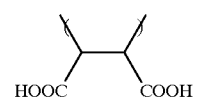

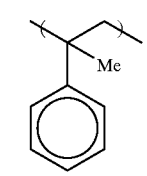

(ii) dispersing said formulation in an aqueous medium.

An agricultural formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II.

53 Claims, No Drawings

METHOD AND COMPOSITION

The present invention relates generally to dispersants, for use in agricultural applications, in particular the present invention relates to methods for the dispersion of insoluble material with copolymeric dispersants which dispersions are formed with improved dispersibility and show improved suspensibility. The present invention also relates to methods of producing dispersible formulations, the formulations per se and methods of treating substrates with dispersions produced from such formulations.

The active principles in many agricultural applications are largely hydrophobic or water insoluble in character and are, by necessity, often administered as finely divided solids suspended in aqueous media. The majority of these active principles are manufactured and marketed in concentrated form, possibly with the addition of other insoluble inert fillers, which are then diluted prior to application. For example, the active principle is typically available in the form of a suspension concentrate (SC), wettable powder (WP) or water dispersible granule (WG). However, due to the generally hydrophobic nature of the active principle, the addition of a suitable dispersant is essential in order to achieve an homogenous dispersion with a minimum of mixing, such as may be achieved readily by hand or with minimal mechanical mixing. Furthermore, once an homogenous dispersion is achieved, the resulting suspension must remain stable for a time sufficient, at least, to allow application by usual means such as spraying. Any settling, agglomeration or flocculation of the finely divided solid may lead to inconsistent and ineffective application as well as blockage of the spraying equipment. It is therefore necessary to provide a dispersant which provides easy and homogenous dispersion and results in a suspension which maintains its stability during the application of the aqueous dispersion.

Effective dispersants for use in these applications ideally provide a suspension with acceptable dispersibility, suspensibility and lack of agglomeration. The Collaborative International Pesticides Analytical Council (CIPAC Handbook Volume 1) defines methods that can be used for determining acceptable suspensibility (MT 15.1) and degree of agglomeration (MT 59.3). For example, in suspension concentrates so-called SC formulations, this can be achieved by the addition of about 3–5 w/w % of a standard dispersant. Wettable powder (WP) and water dispersible granule (WG) formulations generally require the addition of standard dispersant in the order of 6–7 w/w % in order to achieve acceptable suspensibility and degree of agglomeration as determined by a wet sieve retention test. (MT 59.3).

Currently used dispersants for SC formulations include ethylene oxide/propylene oxide block copolymer surfactants based on an hydrophobic moiety plus ethyleneoxide. Also used are ether phosphate derivatives of non-ionic surfactants, especially of tristyrylphenol ethoxylates. Conventional anionic surfactants used include sulphonated derivatives of arylformaldehyde condensates, polyacrylates and lignosulfonates.

Dispersants for WP and WG formulations are usually limited by the requirement that the dispersant be solid at ambient temperatures, be non-gelling and not dissolve the active principle. For these reasons, conventional non-ionic surfactants are often unsuitable, and anionic dispersants are preferred. Known effective dispersants for WP and WG formulations include sulphonated alkylnaphthalene/formaldehyde condensate salts and lignosulfonate salts.

α-Olefin-polycarboxylate copolymers are well known as dispersants in a wide range of applications including pigment dispersion, emulsion polymerisation, cosmetics and pesticidal compositions. As far back as 1972 the sodium salt of a maleic anhydride and diisobutylene copolymer was given an exemption from tolerance for use in pesticide formulations by the United States Environmental Protection Authority following a petition from Rohm and Haas Co. FR 2545325 describes the use of ammonium and alkali metal salts of maleic anhydride-diisobutylene copolymer in pesticide granules. Similarly, EP 201417 describes the use of copolymers of maleic anhydride with surfactants selected from sulfates and phosphates of ethoxylated phenol derivatives in WP and WG formulations. JP 62036302 describes copolymers having a molecular weight range of from 5000–20000 for use with granular agrochemical compositions. Maleic anhydride and diisobutylene copolymer derivatives are described for use in conjunction with $CaCO_3$ and Mg salts for SC formulations in JP 06 09,302. The use of sulfonated derivatives of copolymers of maleic anhydride in water dispersable granules is also described in JP 58-131903.

French Patent No. 2,397,444 describes stable and concentrated dispersions of active materials which may be prepared from non-dusting powders or granular materials. It is necessary to separate the active material in the presence of a salt of an acidic resin, such as, for example, a copolymer of maleic anhydride and an α-olefinic compound; add an organic solvent which forms, together with the aqueous medium, a two-phase system; treat such two-phase system by adding a carrier substance thereto; and then isolate the product by a reduction in the volume of the organic phase by the addition of water, the solvent gradually transferring into the added water.

We have now found that the use of derivatives of an alternating copolymer of α-methyl styrene and maleic anhydride provides surprisingly improved dispersibilty and suspensibility in agrochemical formulations, as well as a number of other ancillary benefits which will be more fully described herein.

According to a first aspect of the present invention, there is provided a method of dispersing an insoluble material in an aqueous solution comprising the following steps:

(i) providing a formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and

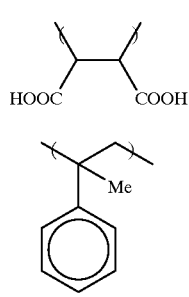

(ii) dispersing said formulation in an aqueous medium.

According to a second aspect of the present invention, there is provided a method of making an agrochemical formulation comprising the steps of:

(i) combining at least one insoluble material, and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II in an aqueous medium;

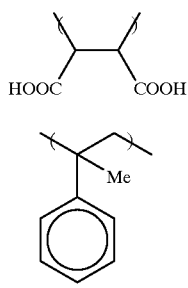

(ii) milling said combination to a particle size range in order to obtain a stable, readily-suspendible aqueous dispersion; and
(iii) stabilising said aqueous dispersion to obtain an SC formulation suitable for dilution in water for agricultural use.

According to a third aspect of the present invention, there is provided a method of making an agrochemical formulation comprising the steps of:
(i) combining at least one insoluble material, with at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and

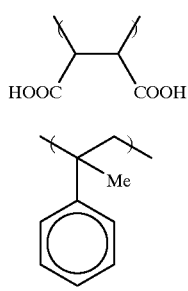

(ii) milling said combination to a desired particle size to obtain a homogeneous wettable powder (WP) formulation.

According to a fourth aspect of the present invention, there is provided a method of making an agrochemical formulation comprising the steps of:
(i) combining at least one insoluble material suitable for agricultural use with at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and

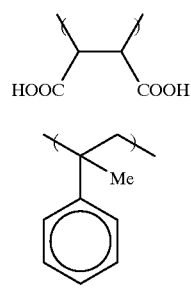

(ii) blending said combination to obtain a homogeneous wettable powder (WP) formulation.

According to a fifth aspect of the present invention, there is provided a method of making an agrochemical formulation comprising the steps of:
(i) combining at least one insoluble material suitable for agricultural use with at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II;

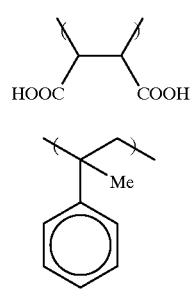

(ii) agglomerating said combination to form discrete granular materials; and
(iii) drying said granular materials to obtain a water dispersible granule WG formulation.

According to a sixth aspect of the present invention, there is provided a formulation produced by the process of the second, third, fourth and fifth aspects.

According to a seventh aspect of the present invention, there is provided an agricultural formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II.

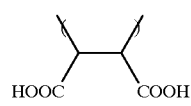

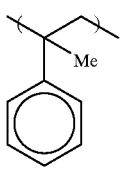

According to an eighth aspect of the present invention, there is provided a method of treatment of a substrate with a insoluble material comprising the following steps:

(i) preparing a formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II;

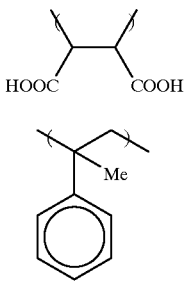

(ii) dispersing said formulation in an aqueous medium; and (iii) applying the dispersed formulation to a substrate.

The dispersants for use in the present invention are based on alternating copolymers. It will be understood by those skilled in the art that alternating copolymers may be prepared by the careful selection of comonomers and reaction conditions. As is well known in the art, often additional polymerization conditions should be observed in order to obtain an alternating copolymer. For example the temperature and type of solvent can influence whether an alternating or other type of copolymer is formed. Methods for making such alternating copolymers having first and second comonomer residues according to formulae I and II respectively will be well known to those skilled in the art of polymer synthesis.

The alternating, or substantially alternating character, of the copolymers is believed to be of importance to the present invention. The person skilled in the art will understand the degree of regularity necessary in order for a copolymer to be considered of alternating character. It is preferred that the alternating copolymer has an alternating character defined by greater than 70% of consecutive comonomer residue units being alternate between residues of the first comonomer and the second comonomer, more preferably greater than 90%. A high degree of control in the synthesis of such copolymers is required in most cases to achieve this.

The alternating copolymer may contain additional comonomer residues. For example, the addition of a small amount, say less than 10%, of methyl methacrylate will not substantially change the alternating character of the copolymer. Suitable alternating copolymers for use in the present invention also include copolymers of three or more comonomers. While not wishing to be bound by theory it appears that where a consistent hydrophobic polymer backbone is provided in the presence of regularly spaced anionic charge along the polymer molecule such as obtained by an alternating copolymer, the improved dispersant performance is obtained.

While not wishing to be bound by theory, it is believed that the stiffness of the polymer molecule is related to its performance as a dispersant. It is believed that improved dispersant performance is related to the degree of steric hindrance and thereby resistance of the copolymer to free rotation.

The dispersants are agriculturally acceptable salts or water-soluble agriculturally acceptable derivatives of the alternating copolymer and are preferably readily soluble in water. Suitable salts include alkali metal salts such as the sodium or potassium salt of the alternating copolymer. Ammonium salts of the alternating copolymer may be used, however some ammonium salts which contain significant levels of by-products appear to have some limitations on their use since they have been found to be unsuitable in some WG formulations. While not wishing to be bound by theory, it is believed that they appear to disintegration of the granule and lead to formation of non-dispersing aggregates. While agriculturally acceptable salts of the alternating copolymer are generally preferred, the alternating copolymer may be provided in the formulation in addition to a source of suitable cations where the addition of the cation source to aqueous media solubilises the alternating copolymer.

Preferably the amount of suitable cations is sufficient to provide optimum dispersant characteristics in the alternating copolymer. It is generally desirable to provide an excess of cations such that a substantial amount of the alternating copolymer forms polyanionic polymer.

The anhydride of the alternating copolymer is not generally soluble in water. However, we have found that the free acid shows a degree of solubility in water. In one embodiment the formulation may contain the free acid of the alternating copolymer (in the absence of any suitable cation source). A cation source may be provided in a separate addition to the aqueous medium prior to the dispersing of the formulation.

We have found that certain combinations of free acids of the alternating copolymer with separate addition of a cation source prior to dispersing the formulation are advantageous. It is believed that the reaction between the free acid and the cation source generates gas and the action of which facilitates the disintegration of the granule containing the insoluble material. In particular, the addition of sodium carbonate leads to the generation of carbon dioxide and results in improved disintegration of the granule. Other cation sources may be selected so as to generate a variety of gaseous reaction products to provide improved dispersion.

Cation sources suitable for incorporation into either the formulation or the aqueous medium include sources of agriculturally acceptable cations, such as alkali metal cations. Preferably the cation source is selected from the group consisting of alkaline salts such as carbonates, bicarbonates, hydroxides, phosphates, alkoxides, borates, sulphites and silicates. Other water soluble agriculturally acceptable derivatives of the alternating copolymer include polyethyleneoxy derivatives, polyethyleneglycol derivatives, polyamide derivatives and polyvinyl alcohol derivatives. By water-soluble it is meant that the derivatives of the alternating copolymer are at least partially water-soluble at ambient temperatures. Other water-soluble derivatives of the alternating copolymer are also useful in the present invention.

The preferred molecular weights of the alternating copolymers are in the range of from 1000 to 90000 daltons. We have found that certain higher molecular weight alternating copolymers show a certain degree of intractability in solution and our more preferred range is from 10,000–40,000 daltons.

We have found that agriculturally acceptable salts of alternating copolymers as described herein for use as dispersants in agricultural compositions provide improved and consistent dispersant performance when compared to conventionally used dispersants such as sulphonated alkylnaphthalene formaldehyde condensate salts.

It is surprising that agriculturally acceptable salts of alternating copolymers as described herein give enhanced performance when compared to previously described preferred structures in the prior art such as for example diisobutylene isobutylene and styrene copolymers with maleic anhydride while still other derivatives described in those same publications, cannot be reasonably used as dispersants in agricultural applications at all. For example we have found that some styrene-maleic anhydride copolymer derivatives resulted in less stable and sometimes unstable dispersion. Similarly some linear α-olefin maleic anhydride derivatives such as those derived from n-octene and n-decene also yielded unstable dispersions affording poor suspensibility.

The performance of the agriculturally acceptable salts of alternating copolymers described herein can also be compared to diisobutylene derivatives by comparing the suspensibility observed at different dispersant concentrations in WP and WG formulations. The lower the dispersant concentration at which an acceptable suspensibility result remains, the more efficient is the surface coverage of the dispersant. In practical terms this means the dispersant will be more cost effective to the end user. When the use rate of agriculturally acceptable salts of alternating copolymers of the present invention is compared to that of a diisobutylene maleic anhydride sodium salt of similar molecular weight we have found that the agriculturally acceptable salts of alternating copolymers of this invention may give acceptable stability at a concentration significantly lower than the corresponding diisobutylene derivative.

Methods for making such alternating copolymers having first and second comonomer residues according to formulae I and II respectively will be well known to those skilled in the art of polymer synthesis.

The dispersant system used in embodiments of the present invention may be a mixture of the alternating copolymer as herein described with other dispersants known to those skilled in the art, including alkyl substituted and unsubstituted sulfonated naphthalene formaldehyde condensate salts, alkyl substituted and unsubstituted phenol formaldehyde condensate salts, lignosulphonate salts, polyacrylate salts, and other olefin-unsaturated carboxylic acid copolymer derivatives.

In agrochemical applications, a wide variety of insoluble materials such as active principals are delivered in aqueous suspension. Active principals such as those used in WP, WG and SC formulations are generally insoluble at ambient temperatures. Water insoluble materials which may advantageously be used in WP, WG and SC formulations include herbicides, insecticides, fungicides, biocides, molluscicides, algaicides, plant growth regulators, anthelmintics, rodenticides, nematocides, acaricides, amoebicides, protozoacides, crop safeners and adjuvants. Examples of such actives commonly granulated or made as powders in agriculture include: triazine herbicides such as simazine, atrazine, terbuthylazine, terbutryn, prometryn and ametryn, urea herbicides such as diuron and fluometron, sulphonyl urea herbicides such as chlorsulfuron, metsulfuron methyl, nicosulfuron and triasuifuron, sulphonanilide herbicides such as flumetsulam, organophosphate insecticides such as azinphos methyl, chlorpyrifos, sulprofos and azamethiphos, carbamate insecticides such as aldicarb, bendiocarb, carbaryl and BPMC, synthetic pyrethroids such as bifenthrin, as well as various types of fungicides including dimethomorph, benomyl, carbendazim, mancozeb, triazoles such as hexaconazole and diniconazole, acaricides such as propargite. A list of such products can be drawn from the Pesticide Dictionary (contained in the Farm Chemicals Handbook) or the British Crop Protection Society. Pesticides Manual.

In addition, some fertilizers and also water soluble active principles may use water dispersible formulations either by addition of inert carriers for convenience in handling or to aid in a controlled release formulation.

A wide variety of other insoluble materials are used in agricultural applications including fillers and carriers, for example but not limited to, natural and synthetic silicates and silicate minerals, mineral oxides and hydroxides and also natural and synthetically derived organic materials. Such materials may be added as porous carriers, as moisture inhibition agents, to aid binding or agglomeration properties of a formulation or simply to fill a formulation to a convenient weight. Examples of such fillers may include natural silicates such as diatomacious earth, synthetic precipitated silicas, clays such as kaolin, attapulgites and bentonites, zeolites, titanium dioxide, iron oxides and hydroxides, aluminium oxides and hydroxides, or organic materials such as bagasse, charcoal, or synthetic organic polymers. These other insoluble materials may be readily dispersed in accordance with the present invention.

An additional agent conventionally used in combination with dispersants used in the above formulations is a surfactant wetting agent. The role of the wetting agent in the case of SC formulations is to aid removal of air from particle surfaces during manufacture and to aid dilution in water. In the case of WP formulations the role of the wetter may be to aid penetration of the solids into water, while in the case of WG formulations it may aid penetration of the granules into water and aid disintegration of granules back to primary particle size. In some cases the dispersant may itself function as a suitable wetting agent while in others the dispersant may show an antagonistic effect on the wetter. As a further embodiment of the present invention at least one surfactant wetting agent may be selected from the group consisting of an alkylpolysaccharide; di or mono alkyl sulphosuccinate derivative; a nonionic surfactant loaded onto an inert silicate carrier; and a non-ionic surfactant delivered in the form of a urea surfactant complex.

The step of dispersing the formulation in an aqueous medium may be achieved by any convenient means dependent on the nature of the formulation. It is desirable that the dispersion of the formulation in an aqueous solution may be conducted either by hand or with a minimum of mechanical agitation. Mechanical agitation may include stirring, mixing, blending and other similar processes.

The suspension of insoluble material in aqueous medium will be typically used for the treatment of a substrate such as plant or other agricultural medium. The application of the suspension onto the substrate may be achieved by any convenient means, including spraying, and the like. Granules are generally dispersed in water prior to being sprayed by the farmer. Farm sprays may be as a small back-pack handspray or a large boom spray or other convenient means. Aerial spraying is also sometimes used.

Formulations of the present invention may also be applied to the substrate directly, prior to dispersion. The subsequent application of rain or other aqueous media is sufficient for the formulation of the suspension of particulate material.

The present invention is described with reference to WP, WG and SC formulations. In each case, formulations provide a stable aqueous dispersion of finely milled insoluble hydrophobic particles. The stability properties of the dispersion and hence the effectiveness of the dispersion can be measured by means of a suspensibility test as described by the CIPAC test MT 15.1. In this test the volume fraction of suspended material is compared to that which has settled out due to gravity after 30 minutes. Typically a dispersant achieving a reported percentage suspensibility about 80% would be considered as an effective dispersant for WG and WP formulations, while in excess of 90% would be expected for an SC formulation. Another measure of the stability of the dispersion is the degree to which particles remain non aggregated. This may also be a property of the even distribution of the dispersant in the formulation. The degree to which particles may be aggregated is often measured by a wet sieve retention test as described in CIPAC test MT 59.3. In this test the dispersed solid is poured through a series of fine sieves and retained material is measured as a fraction of the total amount of dispersed material. Formation of such aggregates is a major problem observed in WG formulations and to a lesser extent in WP formulations.

Generally WP formulations are produced by milling the active principle either alone or in combination with fillers, dispersants and/or surfactant wetters to a suitable average particle size, typically in the 5–15 μm range. The milled material is then dry blended with a surfactant wetter, and/or dispersant if not already present or with additional dispersants and/or surfactant wetters to give a homogeneous composition. The powder formulation is assessed for wettability according to a method such as CIPAC MT 53.5.1 and suspensibility as per CIPAC MT 15.1. A formulation will desirably have a wettability of less than 1 minute and a suspensibility above 80%. Below 60% would generally be considered unacceptable. Results which might be commercially acceptable are either determined by the local registration authority or by the standards set by the formulators themselves.

In the case of WG formulations a suitably milled active ingredient with or without other fillers, typically of average particle size 5 to 15 μm may be mixed with one or more surfactants wetters and one or more dispersants. Typically an excess of water is added to bind the particles together into agglomerates. The excess water is later reduced by suitable air drying techniques to an optimal level.

The agglomerates are typically granulated using one of many techniques including pan granulation, drum granulation, fluid bed granulation, spray drying, tabletting or extrusion techniques which are well known to those skilled in the art.

The wetter and dispersant may either be powder blended with the active ingredient or alternatively blended as an aqueous solution in the water used to aid agglomeration. The active ingredient, fillers, wetter and dispersant may also be milled together in one operation prior to the addition of water.

For a WG formulation to be acceptable an additional requirement is that the said granules should readily disperse in water back to the primary dispersed particle size within a short period. This property is known as dispersibility and in describing the current invention it is measured as the time taken for granules to disperse back to primary particle size in water under a standard degree of agitation. A dispersion time of less than one minute is desirable, 20 seconds is excellent and 2 minutes is poor. Desirably the granules should also have good suspensibility. Suspensibility is typically tested using CIPAC MT 15.1. Above 80% is a desirable result, less than 60% is generally regarded as undesirable. In many cases when testing granules a so-called maximum surface coverage result is often obtained. This is where the suspensibility results reach a maximum level then plateau. Adding more dispersant will not generally improve the result. This phenomenon is thought to be due to the particle size distribution of the material. Usually there is a given number of particles which are of such a size that they will settle regardless of type and concentration of dispersant.

Desirably the granules should have low wet sieve retention. Wet sieve retention is typically tested using CIPAC MT 59.3. For the 150 μm sieve less than 0.1% retained material is desirable. Less than 0.02% is more desirable. Likewise for the 53 μm sieve less than 0.6% is desirable, anything less than this is more desirable.

A further desirable property of a WG formulation is that the granules should be non-dusty and resistant to attrition. This is often a property of the method of granulation used and the level of compaction there obtained. Often there is an observed tradeoff between the dispersibility properties of a WG formulation and the level of compaction and attrition resistance. Attrition resistance may be measured by subjecting granules to a set degree of agitation and measuring the level of smaller particles generated by means of passing through sieves of various sizes, Storage stability may be tested by storage at 50 degrees celsius and tested as above at I month and 3 month intervals to determine if any properties have changed significantly.

Preferably, the granules should maintain these properties on storage. Surprisingly, it has been observed that, upon prolonged storage, solid formulations such as WP and WG formulations containing dispersants such as those described herein are not as susceptible to deterioration in dispersability and suspensibility as formulations of the prior art. Further, it is observed that WG formulations prepared containing dispersants such as those described herein which are prepared by methods, such as extrusion, leading to a high degree of compaction to afford attrition resistance, will still show ready dispersibility.

We have also found that WP and WG formulations which incorporate the dispersants described herein require typically less dispersant, than for presently known WP and WG formulations.

As a further embodiment of the present invention in the case of WP and WG formulations the alternating copolymer dispersants herein described may be combined with surfactant wetting agents selected from the classes comprising alkylpolysaccharides, dialkyl and monoalkylsulphosuccinate salts, nonionic surfactants loaded onto porous silicate carriers and urea surfactant complexes of non-ionic surfactants. The wetting agent may be combined in such formulations at a rate in excess of 1% w/w and preferably less than 3% w/w. Most preferred from the alkylpolysaccharide class of wetting agents are alkylpolyglucosides derived from reaction with glucose and a primary hydrocarbon alcohol. Even more preferred are the highly crystalline derivatives such as obtained from ECOTERIC AS 20 and ECOTERIC AS 10 (Huntsman Corporation Australia Pty Ltd). Most preferred from the monoalkylsulphosuccinate class are sodium or potassium salts of cyclohexyl, iso-octyl and n-octyl sulphosuccinate. Most preferred from the dialkylsulphosuccinate class are sodium or potassium salts of dicyclohexyl, diisooctyl and di-n-octyl sulphosuccinates. Most preferred from the class of nonionic surfactants loaded onto insoluble porous silicate carriers are ethoxylated surfactants loaded onto carriers such as TERIC 157 (Huntsman Corporation Australia Pty Ltd). Most preferred wetting agents from the urea surfactant complexes are urea adducts of alcohol ethoxylate surfactants such as TERWET 7050 (Huntsman Corporation Australia Pty Ltd). The wetters herein described show good wettability and dispersibility for the formulations and have the additional advantage of showing storage stability in combination with the copolymer dispersants described. Whereas by comparison some commonly used WG and WP wetters such as alkylnaphthalene sulphonate salts and lignosulphonate salts have been found to show poor storage stability.

In the case of SC formulations in the present invention an active ingredient is typically added to water containing a dispersant, preferably with a surfactant wetting agent together with a conventional non-ionic dispersant. A humectant may also be included. A dispersion is formed using high shear mixing. The dispersion is then rnilled by any one of several means of wet milling so that the mean particle size of the dispersed solid is below 5 $\mu$m more typically in the range of from 1 to 3 $\mu$m. The resulting product is known as a millbase and may be modified with additives such as antifreeze, thickeners and antisettling agents, biocides and colouring agents may be added. For an SC formulation to be acceptable it should not show a high degree of thickening, settling or growth of aggregates over time. These physical properties can be assessed by visual observation.

SC's generally require good viscosity and storage stability. Storage stability is usually assessed as degree of top settling or syneresis, sedimenting or "claying" which is the tendency to form a sticky layer on the bottom and "bleeding" which is the tendency of the dispersion to separate without necessarily displaying even settling. Redispersibility is also important. These may also be assessed visually.

For SC formulations in the case of dispersants described herein only certain dispersant copolymers are suitable. When used alone, some dispersant copolymer derivatives give a viscosity of slurry premix unsuitable for milling so it is preferable to combine the dispersant with another fast acting well known dispersant such as an EO/PO block co-polymer type dispersant. While not wishing to be bound by theory it appears that the dispersant needs time to migrate to the surface of the dispersed particles. The dispersant copolymers are used synergistically with other known dispersants in some cases.

While the present invention has been described with reference to agrochemnical formulations, it will be apparent that the improvements in dispersibility and suspensibility will render the present invention useful in other applications. The present invention will now be further described with reference to the following non-limiting examples and figures. All percentages recited herein are by weight of the total composition unless otherwise specified.

EXAMPLE 1

A Simazine 900 g/kg WG formulation of the following composition was prepared.

| | |
|---|---|
| Simazine tech. (98% w/w) | 91.8% w/w |
| ATPLUS G73050 | 1.5 |
| (now sold under the Trade Mark TERWET 7050, Huntsman Corporation Australia Pty Ltd) | |

-continued

| | |
|---|---|
| DISPERSANT | 3.1 |
| Kaolin | 3.1 |
| Water | 0.5% |

The dispersant used was the sodium salt of an alternating copolymer of alphamethylstyrene and maleic anhydride of approximate molecular weight 30,000 to 40,000.

The granules were prepared by blending the solids with sufficient weight of water such as to give a plastic premix which was then extruded using a Fuji-Paudal laboratory scale extrusion granulator. The resulting granules were then dried by means of a fluid bed drier back to a water content of approximately 0.5% w/w.

The resulting WG was tested for dispersibility by recording the time in seconds required for total disintegration under uniform agitation. The suspensibility was tested according to CIPAC MT 15.1 and the wet sieve retention was tested using 150 $\mu$m and 53 $\mu$m sieves according to CIPAC MT 59.3. The granules were then placed on storage at 50 degrees celsius for a period of 3 months and the above described tests were repeated after 1 month and 3 months of storage. Results are recorded in TABLE 1.

EXAMPLE 2

A WG formulation was prepared and tested as described in Example 1 with the dispersant used being the sodium salt of a non-alternating 10:3 (mole ratio) alphamethylstyrene:maleic anhydride copolymer of approximate molecular weight 30,000 to 40,000. Results are shown in TABLE 1.

EXAMPLE 3

A WG formulation was prepared and tested as described in Example 1 with the dispersant used being the sodium salt of a non-alternating 4:3 (mole ratio) alphamethylstyrene:maleic anhydride copolymer of approximate molecular weight 30,000–40,000. Results are shown in TABLE 1.

EXAMPLE 4

A WG formulation was prepared and tested as described in Example 1 with the dispersant used being the sodium salt of a non-alternating alphamethylstyrene:maleic anhydride copolymer of approximate molecular weight 30,000–40,000 prepared using a 50% molar excess of maleic anhydride. Results are shown in TABLE 1.

EXAMPLE 5

A WG formulation was prepared and tested as described in Example 1 with the dispersant used being the sodium salt of an alphamethylstyrene:maleic anhydride:methacrylic acid terpolymer of approximate molecular weight 30,000–40,000, prepared using 20 mole percent methacrylic acid. Results are shown in TABLE 1.

EXAMPLE 6

A WG formnulation was prepared and tested as described in Example 1 with the dispersant used being the sodium salt of an alphamethylstyrene:maleic anhydride:methacrylic acid terpolymer of approximate molecular weight 30,000–40,000, prepared using 10 mole percent methacrylic acid. Results are shown in TABLE 1.

EXAMPLE 7

A WG formulation was prepared and tested as described in Example 1 with the dispersant used being the sodium salt of an alphamethylstyrene:maleic anhydride:methacrylic acid terpolymer of approximate molecular weight 30,000–40,000, prepared using 2 mole percent methacrylic acid. Results are shown in TABLE 1.

EXAMPLE 8

A WG formulation was prepared and tested as described in Example 1 with the dispersant used being the sodium salt of a copolymer of alphamethylstyrene and maleic anhydride of approximate molecular weight 30,000–40,000, prepared by a combination of sodium carbonate and free acid of the parent polymer. Results are shown in TABLE 1.

EXAMPLE 9

A WG formulation was prepared and tested as described in Example 1 with the dispersant being a monoammonium salt of an alternating copolymer of alphamethylstyrene and maleic anhydride. Results are shown in TABLE 1.

EXAMPLE 10

A Simazine 900 g/kg WG formulation of the following composition was prepared.

| | |
|---|---|
| Simazine tech. (98% w/w) | 91.8% w/w |
| MORWET EFW | 1.5 |
| (Witco Corp) | |
| DISPERSANT | 6.2 |
| Water | 0.5% |

The dispersant used was an alkylnaphthalene formaldehyde condensate salt, SCS 2258 (ICI Surfactants). The granules were prepared in the manner described in Example 1. The results are shown in TABLE 1.

EXAMPLE 11

A Simazine 900 g/kg WG formulation of the following composition was prepared.

| | |
|---|---|
| Simazine tech. (98% w/w) | 91.8% w/w |
| ATPLUS G73050 | 1.5 |
| (now sold under the Trade Mark TERWET 7050, | |
| Huntsman Corporation Australia Pty Ltd) | |
| DISPERSANT | 6.2 |
| Water | 0.5% |

The dispersant used was a sodium salt of an alternating copolymer of alphamethylstyrene and maleic anhydride of approximate molecular weight 30,000 to 40,000. The granules were prepared and tested in the manner described in Example 1. The results are shown in TABLE 1.

EXAMPLE 12

A Simazine 900 g/kg WG formulation of the following composition was prepared.

| | |
|---|---|
| Simazine tech. (98% w/w) | 91.8% w/w |
| ATPLUS G73050 | 1.5 |
| (now sold under the Trade Mark TERWET 7050, | |
| Huntsman Corporation Australia Pty Ltd) | |
| DISPERSANT | 3.1 |
| Kaolin | 3.1 |
| Water | 0.5% |

The dispersant used was the sodium salt of a 1:1 (mole ratio) copolymer of styrene and maleic anhydride. The granules were prepared and tested in the manner described in Example 1. Results are shown in TABLE 1.

EXAMPLE 13

A Simazine 900 g/kg WG formulation was prepared and tested in the manner described in Example 6 with the dispersant being the sodium salt of a copolymer of n-octene and maleic anhydride of approximate molecular weight 10,000 to 20,000. Results are shown in TABLE 1.

EXAMPLE 14

A Simazine 900 g/kg WG formulation was prepared and tested in the manner described in Example 6 with the dispersant being the sodium salt of a copolymer of n-decene and maleic anhydride of approximate molecular weight 10,000 to 15,000. Results are shown in TABLE 1.

EXAMPLE 15

A Simazine 900 g/kg WG formulation of the following composition was prepared.

| | |
|---|---|
| Simazine tech. (98% w/w) | 91.8% w/w |
| ATPLUS G73050 | 1.5 |
| (now sold under the Trade Mark TERWET 7050, | |
| Huntsman Corporation Australia Pty Ltd) | |
| DISPERSANT | <6.2 |
| Kaolin | >0 |
| Water | 0.5 | where the dispersant used was the sodium salt an alternating copolymer of alphamethyl styrene and maleic anhydride of approximate molecular weight 30,000 to 40,000, used at 3.72% w/w and kaolin was used at 2.48% w/w (ie 60% of normal use rate). The granules were prepared and tested in the manner described in Example 1. Results are shown in TABLE 1.

EXAMPLE 16

A simazine 900 g/Kg WG formulation was prepared and tested as in Example 15 where the dispersant was the sodium salt of an alternating copolymer of alphamethylstyrene and maleic anhydride used at 3.41% w/w and kaolin was used at 2.79% w/w. Results are shown in TABLE 1.

EXAMPLE 17

A simazine 900 g/Kg WG formulation was prepared and tested as in Example 15 where the dispersant was the sodium salt of a copolymer of diisobutylene and maleic anhydride of approximate molecular weight 30,000 to 40,000, used at 6.2% w/w and kaolin was used at 0% w/w. Results are shown in TABLE 1.

EXAMPLE 18

A simazine 900 g/Kg WG formulation was prepared and tested as in Example 15 where the dispersant was the sodium salt of a copolymer of diisobutylene and maleic anhydride used at 5.27% w/w and kaolin was used at 0.93% w/w. Results are shown in TABLE 1.

EXAMPLE 19

A simazine 900 g/Kg WG formulation was prepared and tested as in Example 15 where the dispersant was the sodium salt of a copolymer of diisobutylene and maleic anhydride used at 4.34% w/w and kaolin was used at 1.86% w/w. Results are shown in TABLE 2.

EXAMPLE 20

A simazine 900 g/Kg WG formulation was prepared and tested as in Example 15 where the dispersant was the sodium salt of a copolymer of diisobutylene and maleic anhydride used at 4.03% w/w and kaolin was used at 2.17% w/w. Results are shown in TABLE 2.

EXAMPLE 21

A simazine 900 g/Kg WG formulation was prepared and tested as in Example 15 where the dispersant was the sodium salt of a copolymer of diisobutylene and maleic anhydride used at 3.72% w/w and kaolin was used at 2.48% w/w. Results are shown in TABLE 2. These granules still show good suspensibility.

EXAMPLE 22

A simazine 900 g/Kg WG formulation was prepared and tested as in Example 15 where the dispersant was the sodium salt of a copolymer of diisobutylene and maleic anhydride used at 3.41% w/w and kaolin was used at 2.79% w/w. Results are shown in TABLE 2.

EXAMPLE 23

A Simazine 900 g/kg WP formulation of the following composition was prepared.

| | |
|---|---|
| Simazine tech. (98% w/w) | 91.8% w/w |
| ATPLUS G73050 (now sold under the Trade Mark TERWET 7050, Huntsman Corporation Australia Pty Ltd) | 1.5 |
| DISPERSANT | 3.1 |
| Kaolin | 3.4 | where the dispersant used was the sodium salt an alternating copolymer of alphamethyl styrene and maleic anhydride. Results are shown in TABLE 2. The wettability of the WP was also measured according to CIPAC test MT 53.5.1 and found to be 61 seconds.

EXAMPLE 24

An Atrazine 900 g/kg WG formulation of the following composition was prepared.

| | |
|---|---|
| Atrazine tech. (98% w/w) | 91.8% w/w |
| ATPLUS G73050 (now sold under the Trade Mark TERWET 7050, Huntsman Corporation Australia Pty Ltd) | 1.5 |
| DISPERSANT | 3.1 |
| Kaolin | 3.1 |
| Water | 0.5 | where the dispersant used was the sodium salt of an alternating copolymer of alphamethylstyrene and maleic anhydride. The granules were made and tested as described in example 1. Results are shown in TABLE 3.

EXAMPLE 25

A Diuron 900 g/kg WG formulation of the following composition was prepared.

| | |
|---|---|
| Diuron tech. (97% w/w) | 92.8% w/w |
| ATPLUS G73050 (now sold under the Trade Mark TERWET 7050, Huntsman Corporation Australia Pty Ltd) | 1.5 |
| DISPERSANT | 5.2 |
| Water | 0.5 | where the dispersant used was the sodium salt of an alternating copolymer of alphamethylstyrene and maleic anhydride. The granules were made and tested as described in example 1. Results are shown in TABLE 3.

EXAMPLE 26

A Simazine 900 g/kg WG formulation of the following composition was prepared.

| | |
|---|---|
| Simazine tech. (98% w/w) | 91.8% w/w |
| WETTER | 1.5 |
| DISPERSANT | 6.2 |
| Water | 0.5 | where the dispersant used was the sodium salt an alternating copolymer of alphamethyl styrene and maleic anhydride used at 6.2% w/w, the wetting agent was the sodium salt dicyclohexylsulphosuccinate used at 1.5% w/w and kaolin was used at 0% w/w. The granules were prepared in the manner described in example 1. Results are shown in TABLE 4.

EXAMPLE 27

A Simazine 900 g/Kg WG formulation was prepared and tested as described in Example 26 excepting that the wetting agent used was the sodium salt of monocyclohexylsulphosuccinate used at 1.5% w/w. The granules were prepared in the manner described in example 1. Results are shown in TABLE 4.

EXAMPLE 28

A Simazine 900 g/Kg WG formulation was prepared and tested as described in Example 26 excepting that the wetting agent used was ECOTERIC AS 20 (Huntsman Corporation Australia Pty Ltd), an alkylpolysaccharide used at 1.5% w/w on active strength. (The product comes as a 50% solution in water.) The results are shown in TABLE 4.

EXAMPLE 29

A Simazine 900 g/Kg WG formulation was prepared and tested as described in Example 26 excepting that the wetting agent used was TERIC 157 (Huntsman Corporation Australia Pty Ltd) a nonionic wetter loaded onto an insoluble porous carrier used at 1.5% w/w. The results are shown in TABLE 4.

EXAMPLE 30

A Simazine 900 g/Kg WG formulation was prepared and tested as described in Example 26 excepting that the wetting agent used was MORWET EFW (Witco Corp) a sulphonated aromatic based wetter at 1.5% w/w. The results shown in TABLE 1.

EXAMPLE 31

An Atrazine 900 g/Kg SC formulation of the following composition was prepared.

| | |
|---|---|
| Atrazine tech. 97% w/w | 51.5% w/v |
| Monoethylene glycol | 4.0 |
| ATLOX 4896A | 3 |
| (now sold under the Trade Mark TERSPERSE 4896, Huntsman Corporation Australia Pty Ltd) | |
| DISPERSANT | 2 |
| Silicone antifoam | 0.2 |
| Rhodopol 23 | 0.2 |
| Proxel GXL 20 | 0.1 |
| Water. | 55.0 |

The dispersant used was the sodium salt of an alternating copolymer of alpha methyistyrene and maleic anhydride.

The SC was prepared by dissolving the monoethylene glycol, ATLOX 4896A (now sold under the Trade Mark TERSPERSE 4896, Huntsman Corporation Australia Pty Ltd) and DISPERSANT in 85% of the water and adding the Atrazine tech. and antifoam with vigorous mixing to form a slurry or millbase premix. The premix is then milled using a Dynomill laboratory scale bead mill to give a suitable particle size distribution of >98% of particles below 5 $\mu$m. The millbase thus obtained was then blended with Proxel GXL 20 (Zeneca plc) and Rodopol 23 (Rhodia Inc.) in a premix and then made up to the desired volume with the remaining water and mixed to a homogeneous mixture. The SC thus obtained was of usable viscosity and was found to be storage stable after storage at 2 degrees celsius and 50 degrees celsius for one month, with minimal syneresis and thickening and no claying, sedimentation or aggregates being observed.

EXAMPLE 32

It was attempted to make an SC formulation according to the formula of example 31 with 4% w/w of the sodium salt of an alternating copolymer of alphamethyl styrene and maleic anhydride and only 1% w/w ATLOX 4896A (now sold under the Trade Mark TERSPERSE 4896, Huntsman Corporation Australia Pty Ltd) being used. the resulting millbase premix was of a viscosity which would not allow it to be milled

TABLE 1

| EXAMPLE NO. | DISPERSIBILITY (seconds) | | | SUSPENSIBILITY (%) | | | WET SIEVE RETENTION % | | | | | |
|---|---|---|---|---|---|---|---|---|---|---|---|---|
| | | | | | | | 150 $\mu$m | | | 53 $\mu$m | | |
| | $T_0$ | $T_1$ | $T_3$ | $T_0$ | $T_1$ | $T_3$ | $T_0$ | $T_1$ | $T_3$ | $T_0$ | $T_1$ | $T_3$ |
| 1 | 78 | 70 | 72 | 83 | 86 | 86 | 0.02 | 0.01 | 0.01 | 0.08 | 0.09 | 0.096 |
| 2 | 40 | | | 56 | | | 3.01 | | | 2.49 | | |
| 3 | >120 | | | 77 | | | 3 | | | 1.7 | | |
| 4 | >180 | | | 40 | | | 14 | | | 8.5 | | |
| 5 | 50 | 59 | | 85 | 84 | | 0.006 | 0.01 | | 0.12 | 0.08 | |
| 6 | 43 | 56 | | 81 | 80 | | 0.02 | 0.56 | | 0.2 | 1.11 | |
| 7 | 37 | 48 | | 81 | 71 | | 0.01 | 1.81 | | 0.38 | 2.64 | |
| 8 | 35 | 59 | | 85 | 86 | | 0.007 | 0.02 | | 0.07 | 0.14 | |
| 9 | 81 | 130 | | 83 | 85 | | 0.005 | 0.002 | | 0.05 | 0.01 | |
| 10 | 52 | | 34 | 82 | | 63 | 0.017 | | 0.055 | 0.041 | | 0.89 |
| 11 | 68 | | 56 | 89 | | 88 | 0.015 | | 0.025 | 0.15 | | 0.09 |
| 12 | 55 | | | 31 | | | 0.027 | | | 0.095 | | |
| 13 | 36 | | | 39 | | | | | | | | |
| 14 | 33 | | | 59 | | | 0.002 | | | 0.042 | | |
| 15 | 85 | 75 | 70 | 83 | 86 | 85 | 0.02 | 0.01 | 0.014 | 0.09 | 0.08 | 0.091 |
| 16 | 74 | 67 | 70 | 85 | 84 | 86 | 0.01 | 0.015 | 0.01 | 0.04 | 0.15 | 0.23 |
| 17 | 69 | 65 | 60 | 86 | 85 | 85 | 0.04 | 0.026 | 0.022 | 0.2 | 0.16 | 0.19 |
| 30 | 50 | 41 | 42 | 84 | 68 | 60 | 0.015 | 0.081 | 0.62 | 0.033 | 4.1 | 4.2 |

\* $T_0$ initial results
$T_1$ after 1 month storage at 50° C.
$T_3$ after 3 months storage at 50° C.

TABLE 2

| EXAMPLE NO. | DISPERSIBILITY (seconds) | SUSPENSIBILITY (%) | WET SIEVE RETENTION 150 lm | 53 lm |
|---|---|---|---|---|
| 18 | 58 | 87 | 0.02 | 0.23 |
| 19 | 62 | 86 | 0.02 | 0.21 |
| 20 | 51 | 83 | 0.042 | 0.19 |
| 21 | 56 | 82 | 0.02 | 0.18 |
| 22 | 60 | 72 | 0.02 | 0.15 |
| 23 | | 86 | 0.02 | 0.1 |

\* $T_0$ initial results only

TABLE 3

| EXAMPLE NO. | DISPERSIBILITY (seconds) | SUSPENSIBILITY (%) | WET SIEVE RETENTION 150 lm | 53 lm |
|---|---|---|---|---|
| 24 | 30 | 88 | 0.09 | 0.6 |
| 25 | 40 | 79 | 0.012 | 0.26 |

\* $T_0$ initial results only

TABLE 4

| EXAMPLE NO. | WETTING AGENT | DISPERSIBILITY $T_0$ | $T_1$ | SUSPENSIBILITY $T_0$ | $T_1$ | WET SIEVE RETENTION (%) 150 lm $T_0$ | $T_1$ | 53 lm $T_0$ | $T_1$ |
|---|---|---|---|---|---|---|---|---|---|
| 26 | dicylohexylsulphosuccinate sodium salt | 68 | 56 | 88 | 87 | 0.065 | 0.025 | 0.15 | 0.089 |
| 27 | monocyclohexyl sulphosuccinate sodium salt | 70 | \* | 78 | \* | 0.014 | \* | 0.09 | \* |
| 28 | Ecoteric AS20 | 60 | 61 | 85 | 84 | 0.029 | 0.025 | 0.075 | 0.08 |
| 29 | TERIC 157 | 61 | 63 | 86 | 86 | 0.041 | 0.02 | 0.2 | 0.24 |

\* $T_0$ initial results
$T_1$ after 1 month storage at 50° C.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

What is claimed is:

1. A method of dispersing an insoluble material in an aqueous solution comprising the following steps:

(i) providing a formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and

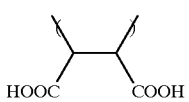

I (ii) dispersing said formulation in an aqueous medium.

2. A method according to claim 1 wherein the alternating copolymer has an alternating character defined by greater than 70% of consecutive comonomer residue units being alternate between residues of the first comonomer and the second comonomer.

3. A method according to claim 1 wherein the alternating copolymer has an alternating character defined by greater than 90% of consecutive comonomer residue units being alternate between residues of the first comonomer and the second comonomer.

4. A method according to claim 1 wherein the alternating copolymer contains additional comonomer residues which will not substantially change the alternating character of the copolymer.

5. An agricultural formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II.

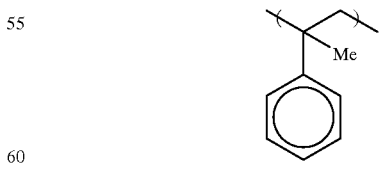

6. An agricultural formulation according to claim 5 wherein the formulation is in the form of a suspension concentrate (SC), a wettable powder (WP) or a water dispersible granule (WG).

7. An agricultural formulation according to claim 5 wherein the alternating copolymer has an alternating character defined by greater than 70% of consecutive comonomer residue units being alternate between residues of the first comonomer and the second comonomer.

8. An agricultural formulation according to claim 5 wherein the alternating copolymer has an alternating character defined by greater than 90% of consecutive comonomer residue units being alternate between residues of the first comonomer and the second comonomer.

9. An agricultural formulation according to claim 5 wherein the alternating copolymer contains additional comonomer residues which will not substantially change the alternating character of the copolymer.

10. An agricultural formulation according to claim 5 wherein the dispersant is an agriculturally acceptable salt of the alternating copolymer and wherein the salt comprises sodium, potassium and/or ammonium ions.

11. An agricultural formulation according to claim 5 wherein the alternating copolymer is in the form of its free acid.

12. An agricultural formulation according to claim 11 further including a cation source.

13. An agricultural formulation according to claim 12 wherein the free acid form of the alternating copolymer and the cation source are capable of reacting to generate a gas.

14. An agricultural formulation according to claim 5 wherein the dispersant is a water-soluble agriculturally acceptable derivative of the alternating copolymer wherein said derivative is selected from the group consisting of polyethyleneoxy derivatives, polyethyleneglycol derivatives, polyamide derivatives and polyvinyl alcohol derivatives.

15. An agricultural formulation according to claim 5 wherein alternating copolymers are in the range of from 1000 to 90000 daltons.

16. An agricultural formulation according to claim 5 wherein the water-insoluble materials are selected from the group consisting of herbicides, insecticides, fungicides, biocides, molluscicides, algaicides, plant growth regulators, anthelmintics, rodenticides, nematocides, acaricides, amoebicides, protozoacides, fertilizers, crop safeners, fillers and carriers and other adjuvants.

17. An agricultural formulation according to claim 5 wherein the formulation further comprises a surfactant wetting agent.

18. An agricultural formulation according to claim 17 wherein the surfactant wetting agent is selected from the group consisting of an alkylpolysaccharide; di or mono alkyl sulphosuccinate derivative; a nonionic surfactant loaded onto an inert silicate carrier; and a non-ionic surfactant delivered in the form of a urea surfactant complex.

19. A method of making an agrochemical formulation comprising the steps of:
(i) combining at least one insoluble material, and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II in an aqueous medium;

20. A method according to claim 19 comprising the steps of:
(i) combining at least one insoluble material, and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II in an aqueous medium;

(ii) milling said combination to a particle size range in order to obtain a stable, readily-suspendible aqueous dispersion; and
(iii) stabilising said aqueous dispersion to obtain an SC formulation suitable for dilution in water for agricultural use.

21. A method according to claim 19 comprising the steps of:
(i) combining at least one insoluble material, with at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and (ii) milling said combination to a desired particle size to obtain a homogeneous wettable powder (WP) formulation.

22. A method according to claim 19 comprising the steps of:
(i) combining at least one insoluble material suitable for agricultural use with at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II; and

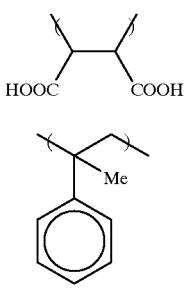

(ii) blending said combination to obtain a homogeneous wettable powder (WP) formulation.

23. A method according to claim 19 comprising the steps of:
(i) combining at least one insoluble material suitable for agricultural use with at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II;

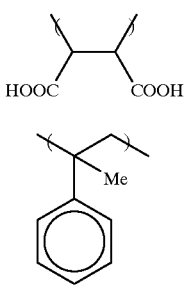

(ii) agglomerating said combination to form discrete granular materials; and
(iii) drying said granular materials to obtain a water dispersible granule WG formulation.

24. A method according to claim 19 wherein the alternating copolymer has an alternating character defined by greater than 70% of consecutive comonomer residue units being alternate between residues of the first comonomer and the second comonomer.

25. A method according to claim 19 wherein the alternating copolymer has an alternating character defined by greater than 90% of consecutive comonomer residue units being alternate between residues of the first comonomer and the second comonomer.

26. A method according to claim 19 wherein alternating copolymer contains additional comonomer residues which will not substantially change the alternating character of the copolymer.

27. A method according to claim 19 wherein the dispersant is an agriculturally acceptable salt of the alternating copolymer and wherein the salt comprises sodium, potassium and/or ammonium ions.

28. A method according to claim 19 wherein the alternating copolymer is in the form of its free acid.

29. A method according to claim 28 further including the step of incorporating a cation source.

30. A method according to claim 29 wherein the free acid form of the alternating copolymer and the cation source are capable of reacting to generate a gas.

31. A method according to claim 19 wherein the dispersant is a water-soluble agriculturally acceptable derivative of the alternating copolymer wherein said derivative is selected from the group consisting of polyethyleneoxy derivatives, polyethyleneglycol derivatives, polyamide derivatives and polyvinyl alcohol derivatives.

32. A method according to claim 19 wherein alternating copolymers are in the range of from 1000 to 90000 daltons.

33. A method according to claim 19 wherein the water-insoluble materials are selected from the group consisting of herbicides, insecticides, fungicides, biocides, molluscicides, algaicides, plant growth regulators, anthelmintics, rodenticides, nematocides, acaricides, amoebicides, protozoacides, fertilizers, crop safeners, fillers and carriers and other adjuvants.

34. A method according to claim 19 wherein the formulation further comprises a surfactant wetting agent.

35. A method according to claim 34 wherein the surfactant wetting agent is selected from the group consisting of an alkylpolysaccharide; di or mono alkyl sulphosuccinate derivative; a nonionic surfactant loaded onto an inert silicate carrier; and a non-ionic surfactant delivered in the form of a urea surfactant complex.

36. A method according to any one of claims 21 to 23 wherein said dispersant achieves a percentage suspensibility of greater than 80%.

37. A method according to claim 20 wherein said dispersant achieves a percentage suspensibility of greater than 90%.

38. A method according to either claim 21 or claim 22 wherein the milling step produces an average particle size in the range of from 5 to 15 μm.

39. A method according to claim 38 wherein the wettable powder has a wettability of less than 1 minute and a suspensibility above 80%.

40. A method according to claim 23 wherein the milling step produces an average particle size in the range of from 5 to 15 μm.

41. A method according to claim 23 wherein the formulation has a dispersion time of less than 1 minute.

42. A method according to claim 23 wherein the formulation has a dispersion time of less than 20 seconds.

43. A method according to claim 23 wherein the formulation has a wet sieve retention for a 150 μm sieve of less than 0.1% retained material and for a 53 μm sieve of less than 0.6%.

44. A method according to claim 23 wherein the milling step produces a mean particle size of less than 5 μm.

45. A method according to claim 23 wherein the milling step produces a mean particle size in the range of from 1 to 3 μm.

46. A method of treatment of a substrate with an insoluble material comprising the following steps:
(i) preparing a formulation comprising at least one insoluble material and at least one dispersant comprising a water soluble agriculturally acceptable derivative of an alternating copolymer or an agriculturally acceptable salt thereof wherein said alternating copolymer comprises at least one first comonomer residue according to formula I and at least one second comonomer residue according to formula II;

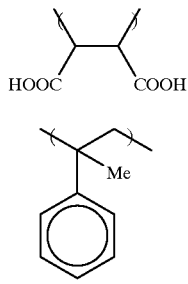

(ii) dispersing said formulation in an aqueous medium; and
(iii) applying the dispersed formulation to a substrate.

47. A method according to claim 46 wherein the alternating copolymer has an alternating character defined by greater than 70% of consecutive comonomer residue units being alternate between residues of the first comonomer and the second comonomer.

48. A method according to claim 46 wherein the alternating copolymer has an alternating character defined by greater than 90% of consecutive comonomer residue units being alternate between residues of the first comonomer and the second comonomer.

49. A method according to claim 46 wherein alternating copolymer contains additional comonomer residues which will not substantially change the alternating character of the copolymer.

50. A method according to claim 46 wherein the dispersant is an agriculturally acceptable salt of the alternating copolymer and wherein the salt comprises sodium, potassium and/or ammonium ions.

51. A method according to claim 46 wherein the alternating copolymer is in the form of its free acid.

52. A method according to claim 46 wherein the dispersant is a water-soluble agriculturally acceptable derivative of the alternating copolymer wherein said derivative is selected from the group consisting of polyethyleneoxy derivatives, polyethyleneglycol derivatives, polyamide derivatives and polyvinyl alcohol derivatives.

53. A method according to claim 46 wherein the water-insoluble materials are selected from the group consisting of herbicides, insecticides, fungicides, biocides, molluscicides, algaicides, plant growth regulators, anthelmintics, rodenticides, nematocides, acaricides, amoebicides, protozoacides, fertilizers, crop safeners, fillers and carriers and other adjuvants.

* * * * *